United States Patent [19]

Zaschel

[11] Patent Number: 5,058,434
[45] Date of Patent: Oct. 22, 1991

[54] PROCESS FOR EARLY DETECTION OF DAMAGE TO MACHINE PARTS

[75] Inventor: Jorg Zaschel, Reuflingen, Fed. Rep. of Germany

[73] Assignee: Carl Schenck AG, Fed. Rep. of Germany

[21] Appl. No.: 485,586

[22] Filed: Feb. 27, 1990

[51] Int. Cl.⁵ ............................................. G01N 29/04
[52] U.S. Cl. ..................................... 73/659; 73/660; 73/584; 340/682
[58] Field of Search ......................... 73/584, 659, 660; 340/682

[56] References Cited

U.S. PATENT DOCUMENTS

| | | | |
|---|---|---|---|
| 3,705,516 | 12/1972 | Reis | 73/659 |
| 3,827,288 | 8/1974 | Fletcher et al. | 73/584 |
| 4,164,149 | 8/1979 | Okubo | 73/664 |
| 4,425,798 | 1/1984 | Nagai et al. | 73/659 |
| 4,615,216 | 10/1986 | Uykoupil | 73/660 |
| 4,724,524 | 2/1988 | Thomas et al. | 73/660 |
| 4,884,449 | 12/1989 | Nishimoto et al. | 73/660 |
| 4,894,644 | 1/1990 | Thomas | 73/660 |
| 4,913,622 | 4/1985 | Uretsky | 73/594 |

FOREIGN PATENT DOCUMENTS

| | | | |
|---|---|---|---|
| 3245505 | 6/1984 | Fed. Rep. of Germany . | |
| 3703429 | 8/1988 | Fed. Rep. of Germany . | |
| 0104883 | 8/1979 | Japan | 340/682 |
| 1367773 | 9/1974 | United Kingdom . | |

OTHER PUBLICATIONS

"Konstruktion" 31 (1979), No. 9, pp. 345 to 351.
"Treunnung von Beanspruchungs-Zeit-Funktionen nach ihrem Ursung" Separation of Stress-time functions according to their source.).
Konstruktion, Band 31, Nr.9,1979 Seiten 345-351, Buxmaum et al., "Trennung von Beanspruchungs-Zeit-Funktionen nach ihrem Ursprung".
Messen und Prudfen/Automatik, Band 10, Nr10, 1974; W. H. Bartak, "SEM-Technik-Gestern Theorie, Heute Bewahrte Praxis".
Siemens-Zeitschrift, Band 48, Nr 9, 1974; p. Ringlage, "Schwingungsanalylse mit dem Proabilitymeter".

Primary Examiner—Hezron E. Williams
Assistant Examiner—Rose M. Finley
Attorney, Agent, or Firm—Connolly and Hutz

[57] ABSTRACT

In a process for early detection of damage top machine parts, particularly rolling element bearings, vibrations are detected by means of a vibration pickup in order to make it possible to describe the present condition of the machine part as well as to estimate the remaining service life of the machine part. The picked-up signals are broken down into periodically determined stochastic and generally stochastic signal components. The signal components for determining the parameters for the stress of the machine part are examined as a function of time and the ascertained stress parameters are compared with characteristics values for the permissible stress of the machine part for purposes of determining the type of damage and/or for determining the extent of the damage.

9 Claims, 2 Drawing Sheets

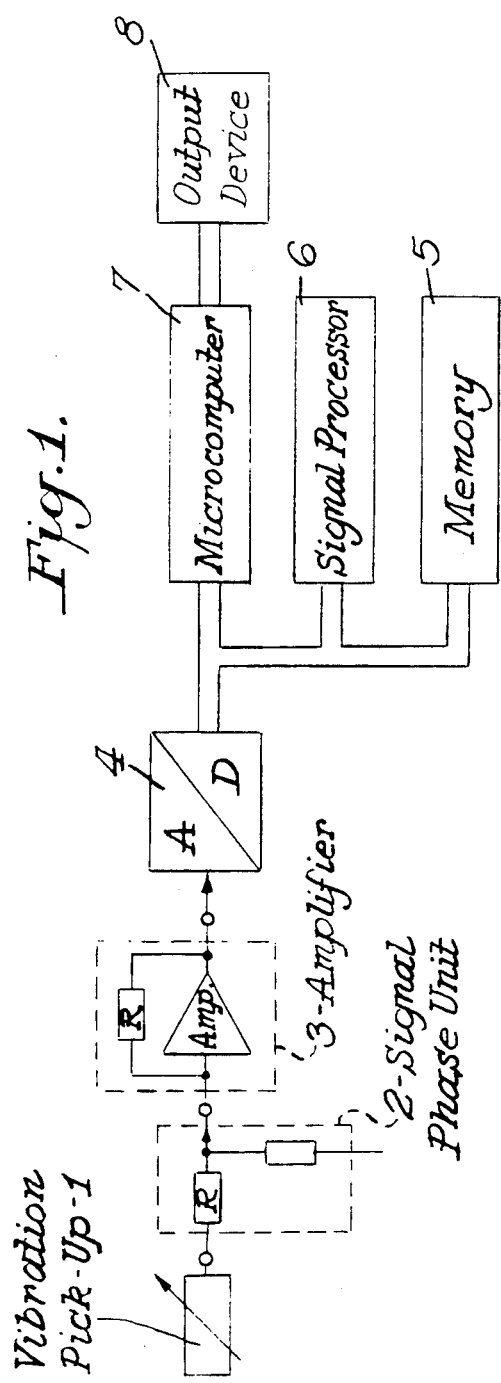
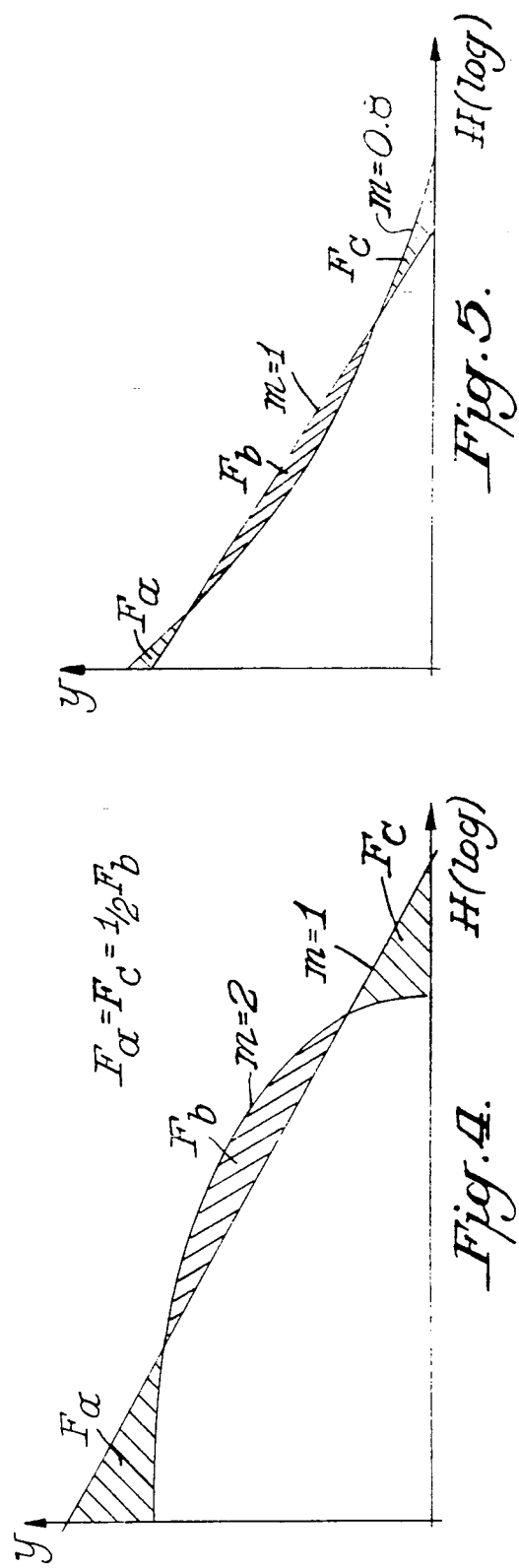

PROCESS FOR EARLY DETECTION OF DAMAGE TO MACHINE PARTS

BACKGROUND OF THE INVENTION

The present invention relates to a process for the early detection of damage to machine parts, particularly rolling element bearings, in which process forced vibrations are detected by means of a vibration pickup.

British Patent No. 1,367,773 discloses a process for the early detection of damage to machine parts, particularly rolling element bearings, in which process signals from forced vibrations stemming from the machine are detected by means of a vibration pickup. Peak values of the forced vibrations always occur whenever a flaw in an otherwise undamaged surface rolls over a second undamaged surface. The picked up signals are transmitted to a peak value detector and to a mean value calculator. By means of a divider, the ratio of the output signal of the peak value detector to the output signal of the mean value calculator is formed and transmitted to a display unit. If the ratio exceeds a preselected limit, a signal is activated. Surface defects can be detected by means of this process, as long as they are still low in number and extent. However, in the case of this process, access to previously measured results is necessary to set the limit values of the ratio.

A process of the type mentioned above, in which forced vibrations of the machine are detected at the machine by means of vibration pickups, is known from West German Patent No. 3,245,505. For this purpose, vibration pickups are used to measure a first structure-borne noise parameter in the high-frequency range and a second structure-borne noise parameter in the low-frequency range of the frequency spectrum, and both measured values are compared by means of a comparator. On the basis of the measured values of the first structure-born noise parameter and of the second body-noise parameter, an auto-performance spectrum $G_{11}$ or $G_{22}$, respectively, is formed for each of these parameters. A cross-performance spectrum $G_{12}$ is also formed calculated on the basis of both structure-borne noise parameters. A coherence function is formed from these values and a rise in the coherence function serves as a signal for the early detection of damage. Although this process makes it possible to carry out early detection of damage independent of the previous determinations of reference values, this process is not suitable for estimating the remaining service life of the machine part.

SUMMARY OF THE INVENTION

Accordingly, an object of the present invention is to make possible early detection of damage which, in addition to a description of the present condition of the machine part, also allows for an estimate of the remaining service life of the machine part.

The invention allows for a reliable evaluation of the present condition of the machine part, especially an early detection of damage, together with an estimate of the remaining service life on an absolute basis. This is accomplished without the need for specific knowledge about previous measurements or a retrieval thereof on the part of the operator, for example, to determine a reference value as is the case with the relative measurements. The evaluation of the present condition according to the invention allows the planning of a stoppage of the production systems, of the power generation equipment or of the other technical installations for purposes of maintenance at appropriate intervals. The invention makes it possible to avoid stoppage costs that arise from unscheduled breakdowns and that amount to far more than the actual repair costs. In order to carry out trend analysis, it is not necessary for comparison purposes to draw up records on the conditions of the machine part in question over the machine's entire service life. As a result, this greatly reduces the effort involved in the maintenance of the machine.

BRIEF DESCRIPTION OF THE DRAWING

Novel features and advantages of the present invention in addition to those mentioned above will become apparent to persons skilled in the art from a reading of the following detailed description in conjunction with the accompanying drawing wherein similar reference characters refer to similar parts and in which:

FIG. 1 is a schematic view of the basic structure of a device for determining early detection of damage according to the invention;

FIGS. 4 and 5 are plots each showing linear distribution in a semilogarithmic representation.

DETAILED DESCRIPTION OF THE INVENTION

Figure 2:
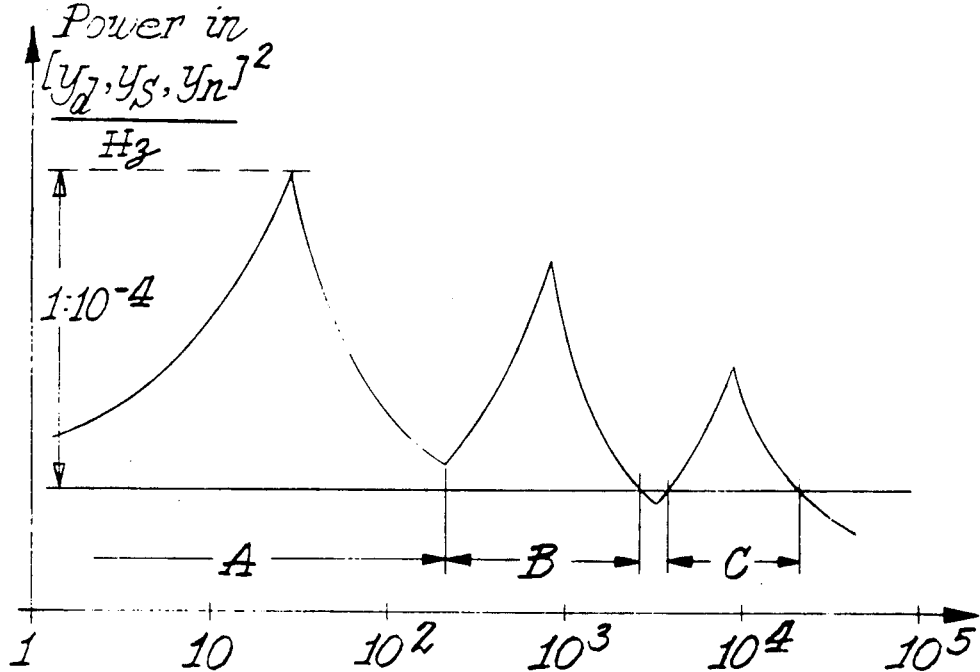
FIG. 2 is a plot of spectral power density as a function of the frequency within defined frequency ranges.

FIG. 1 shows a schematic representation of a device to carry out the process according to the invention. This schematically represented device serves to carry out early detection and evaluation of damage to rolling element bearings. A vibration pickup 1 is arranged to pick up the forced vibrations of the machine when the kinematics are disrupted due to rolling element bearing damage, as well as the inevitable spurious vibrations. In the subsequent signal conditioning unit 2, the measuring signal is adapted in order to be transmitted to the device 3 for further processing, for example, an amplification or attenuation of the measuring signal. In the following preprocessing unit, the signal necessary for further processing, for example, the vibration displacement, is obtained from the measured signal, for example, from the measured acceleration.

In the subsequent analog-digital converter 4, the signal is digitized and stored in the memory 5 for further processing.

By means of the signal processor 6 and the microprocessor 7, the spurious (or noise) signal component is eliminated from the stored signal, which can then be further processed. For this purpose, the measured time function y (t), which contains useful and spurious signals, is compared to a theoretically calculated time function x(t) corresponding only to the useful signal. In order to calculate the time function x(t), the rolling element bearing including the stress mechanism, is arithmetically depicted.

In this process, first of all, a roughness function x is defined as a function of the location along the path of the rolling elements, which is different for the individual types of damage such as, for example, scratches, pitting, cracks or fractures. Taking into account the geometry of the rolling elements and the operating bearing force, the result is a corresponding deformation between the outer bearing race and housing. On the basis of the number of rolling elements and the rotational speed of the rotor, a time-dependent deformation function $x_{A,i}(t)$ results for every location in between the outer race and the bearing housing. Every time function $x_{A,i}(t)$ generates mechanical waves through the bearing housing. The transmission paths from all locations i to a measuring point, for example on the outside of the bearing housing, can preferably be depicted in terms of continuum mechanics in a generally known manner in the form of a transfer function.

At the measuring point, the time function y (t) is picked up, for example, in the form of an acceleration-time function.

By correlating y (t) with the deformation function $x_{A,i}(t)$, the signal components $y_L(t)$ generated by the bearings are determined.

If the dynamic system behavior of the bearings and of the machine is known, then the separation of signal and noise can be accomplished by means of a process of the type described in the journal titled "Konstruktion" 31 (1979), No. 9, pages 345 to 351, "Trennung von Beanspruchungs-Zeit-Funktionen nach ihrem Ursprung" (Separation of stress-time functions according to their source.)

In the case of a dual channel measurement, the noise signals can be eliminated by correlating the measuring signals of both channels, and by differentiating the correlated from the uncorrelated components. Depending on the arrangement of the vibration pickup, the useful signal is assigned to one component or to the other.

The methods mentioned for noise signal elimination can also be combined with each other.

Accordingly, by means of signal processor 6 and microprocessor 7, the useful signal $y_L(t)$ can be broken down in a generally known manner into a determined, periodic component $y_d(t)$, into periodically recurring components with a stochastic amplitude of $y_s(t)$, and into a generally stochastic component $y_n(t)$, for which the following is valid:

$$y(t) = y_d(t) + y_s(t) + y_n(t).$$

These components can be analyzed as a function of the frequency.

For every component $y_d$, $y_s$, $y_n$ of the time function $y_L(t)$, which is picked up at the measuring point and which has had the noise components eliminated from it, the frequency spectrum is determined, preferably in the form of spectral power density. For this purpose, it is practical to determine the frequency ranges by assigning an absolute or relative dynamic range, as illustrated in FIG. 2. The spectral power density is shown in FIG. 2 as a function of the frequency. Moreover, the defined frequency ranges A, B and C are shown. In order to determine the frequency ranges in which each of the evaluations is carrie out, the frequency components that mainly contribute to the intensity are determined. In this process, distortions in the measuring signal caused by the transmission path or by the measuring medium can be corrected in the frequency spectrum, for example, by increasing or decreasing the higher frequencies.

The damage-causing intensities for the determined frequency ranges are ascertained by means of frequency analyses. In this process, the dimensions, extent and form of the frequency distribution are determined. The association of the frequency range in Hz and the statistical frequency distribution produces a stress factor for the rolling element bearing.

Figure 3:
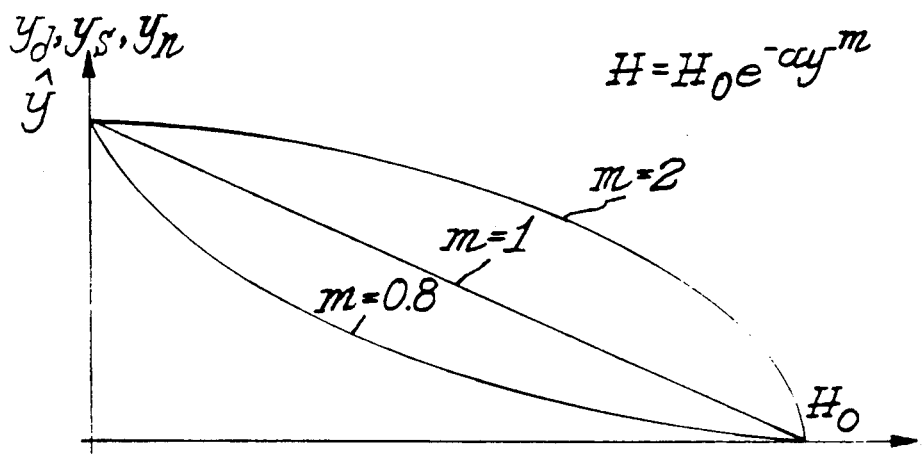
FIG. 3 is a plot of frequency distribution in an amplitude representation.

The frequency distribution of the class boundary deviations is determined for each of these ranges. These frequency distributions are standardized, each still separated for each component $y_d$, $y_s$, $y_n$, as illustrated in FIG. 3. The frequency distributions where m=0.8 and m=2 are then converted into linear distributions for which m=1, as can be seen in greater detail in FIGS. 4 and 5. The equation $F_a = F_c = \frac{1}{2} F_b$ applies to the hatched surfaces in the representation.

The partial surfaces which are encompassed by each of the frequency distributions and by the sought straight line distribution serve as a criterion for the conversion of these frequency distributions with m=0.8 and m=2. There are two intersection points 1 and 2 between these two distributions, seen from the coordinate origin along the abscissa (frequency axis). The surface $F_a$, the surface $F_b$ between 1 and 2, and the surface $F_c$ between 2 and the intersection point of the coordinate distribution with the abscissa are formed by the sections of the frequency distributions m=0.8 or m=2 and the appertaining straight line distribution. For the conversion, $F_a = F_c = \frac{1}{2} F_b$ applies (page 8 of the specification, line 17 through 21, and FIGS. 4 and 5 of the drawing).

Then, for each signal component i and for each frequency range k, the PI (Pattern Intensity) factor $$PI_{i,k} = \frac{\hat{Y}}{RMS} \cdot \frac{\log H_O}{\log (2 \cdot 10^6)}$$

is formed, wherein $\hat{Y}$ is the maximum value of the frequency distribution of each of the signal components y in each of the frequency ranges, RMS is the effective value of each of the signal components y in each of the frequency ranges, and $H_o$ is zero passage number of the frequency distribution. Therefore, summed up over all values k, the result is the component-typical factors $PI_d$, $PI_s$, $PI_n$.

From this sum, the final result is the total PI factor, i.e. the combination of several stress factors, which produce the factor that describes the stress of the rolling element bearing.

A relative damage assessment is calculated by means of known methods of calculating the service life of machine parts that are at risk of damage due to vibration, e.g. the damage-accumulation calculation method according to MINER, which is described in greater detail in the publication of O. Buxbaum, "Betriebsfestigkeit" (Operating Strength), Verlag Stahleisen mbH (publishers), Dusseldorf, West Germany, 1986, Chapter 3. For this purpose, a permissible reference stress typical of the bearing must be given. The permissible reference stress typical of the bearing is represented in the form of a stress-number curve or a service-life line. By continuously observing the extent of the damage over the service life of the rolling element bearing in question, the user is able to estimate the probable remaining service life.

For this purpose, first of all, the stress universe is derived from the data gathered up to that point. This can be done more simply on the basis of the determined PI factors or, more precisely, from the combination of the frequencies determined there.

Each PI factor, multiplied by $\sqrt{2}$ and provided with the appertaining mean frequency, represents a one-stage amplitude universe for which the damage component is calculated. The sum of the damage components for each PI factor results in the sought-after total damage that has occurred up until the point in time under consideration.

In the process according to the invention, the past history is not necessary, as long as the PI factors are below a certain limit value. Beyond that, the history is cumulated to the extent of the damage ascertained at the point in time of the observation. The remaining service life is a direct measure of the remaining operating time, about which assumptions concerning the progress of the damage should be made based on time. These assumptions can be based on generally valid experimental values that have been previously obtained. Therefore, as a rule, trend analysis of the type involved with the known processes is not necessary. The advantage of the process according to the invention lies in the fact that the above-mentioned calculation is carried out on the basis of the stress and is thus directly related to the damage and not, as is the case with the process according to trend analysis, on the basis of the signal. The information provided by the calculated values can, if necessary, even be reinforced by incorporating the PI factors continuously in a trend analysis, but in any case on the basis of the stress.

Moreover, it is possible to draw conclusions about certain types of rolling element bearing damage from the calculated signal components $y_d$, $y_s$ and $y_n$. Local damage is characterized by the presence of all three signal types, whereas in the case of extensive damage such as pitting, grooves, striations or roughness, the signal components $y_s$ and $y_n$ are predominant.

The calibration can be carried out either arithmetically or by means of measuring techniques.

In the case of an arithmetic calibration, the procedure is in principle the same as described above in connection with the arithmetic representation of the rolling element bearing.

In the case of a calibration by means of measuring techniques, during or shortly after start up, measurements are made of a bearing which, in all probability, can be assumed to have no damage. Signals in the form $x_n(t)$ result from these measurements. The basic level e,ovs/y/ of the time function y (t) at the measuring location is detected and stored for further processing. The subsequent evaluation of the measurements is related to this basic level. The same procedure is carried out for the PI factor.

The arithmetic basic stress for each bearing is known from the manufacturer's specifications. Thus, a multiple of the basic level e,ovs/y/ can be converted into a multiple of the basic stress on the bearing. The conversion is done as a function of the total transfer behavior, in other words, the arithmetic representation as explained above, which is linear in the simplest case.

In the device according to FIG. 1, there is an output device 8, which can be in the form of a display, a cathod ray tube or a printer, for displaying measured values or for showing characteristic values.

What is claimed is:

1. A process for early detection of damage to a machine part comprising the steps of detecting vibrations of the machine part by means of a vibration pickup which picks up vibrations of the machine part and transforms them into corresponding picked up signals, breaking down the picked up signals into periodically determined signal components, and periodically recurring components having stochastic amplitudes, examining the signal components for determining the parameters for stress of the machine part as a function of frequency, and using the parameters for stress of the machine part for determining type of damage and/or comparing the parameters for stress of the machine part with characteristic values for permissible stress of the machine part for purposes of determining extent of damage of the machine part.

2. A process as in claim 1 including the steps of digitizing and storing for further processing the signals picked up by the vibration pickup.

3. A process as in claim 2 including the step of, prior to further processing, eliminating spurious and/or noise signal components from the signal that has been picked up.

4. A process as in claim 3 wherein the forced vibrations are picked up in two measuring channels and the spurious and/or noise signals are eliminated by correlating the two picked up signals.

5. A process as in claim 3 wherein the forced vibrations are picked up as a function of time in a measuring channel and compared with a calculated time function containing no spurious and/or noise signal components.

6. A process as in claim 5 including carrying out for preselected frequency ranges frequency analyses of damage-characteristic parameters based on the signal components, and on the basis of the frequency distribution, ascertaining damage-determining intensities which are linked with each individual frequency range for purposes of determining stress parameters.

7. A process as in claim 6 including using at least one of the signal components to ascertain the damage-determining intensities.

8. A process as in claim 7 including subjecting spectral components of the signals picked up by the vibration pickup to a frequency analysis, in which class boundary deviations are determined, standardizing the frequency distributions, converting certain frequency distributions into linear distributions, and determining a component-typical stress parameter for each frequency range.

9. a process as claim 8 wherein the step of determining a component-typical stress parameter for each frequency range further includes summing up the determined component-typical stress parameters to form a total stress parameter.

* * * * *